United States Patent
Hsu et al.

(10) Patent No.: US 9,321,744 B1
(45) Date of Patent: Apr. 26, 2016

(54) METHOD FOR PREPARING 2,5-FURAN DICARBOXYLIC ACID

(71) Applicant: INDUSTRIAL TECHNOLOGY RESEARCH INSTITUTE, Hsinchu (TW)

(72) Inventors: Hsi-Yen Hsu, Hsinchu (TW); Yi-Chang Liu, Tainan (TW); Jyun-Da Wu, Hukou Township (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 14/752,107

(22) Filed: Jun. 26, 2015

(51) Int. Cl.
*C07D 307/36* (2006.01)
*C07D 307/68* (2006.01)

(52) U.S. Cl.
CPC .................................... *C07D 307/68* (2013.01)

(58) Field of Classification Search
CPC ..................................................... C07D 307/36
See application file for complete search history.

(56) References Cited

U.S. PATENT DOCUMENTS

| | | | |
|---|---|---|---|
| 6,063,465 | A | 5/2000 | Charbonneau et al. |
| 6,126,992 | A | 10/2000 | Khanarian et al. |
| 7,385,081 | B1 | 6/2008 | Gong |
| 8,242,292 | B2 | 8/2012 | Yutaka et al. |
| 8,299,278 | B2 | 10/2012 | Gong |
| 8,519,167 | B2 | 8/2013 | Muñoz De Diego et al. |
| 8,524,923 | B2 | 9/2013 | Grushin et al. |

(Continued)

FOREIGN PATENT DOCUMENTS

| | | |
|---|---|---|
| CN | 102648191 A | 8/2012 |
| CN | 102666521 A | 9/2012 |

(Continued)

OTHER PUBLICATIONS

Carlini et al., "Selective oxidation of 5-hydroxymethyl-2-furaldehyde to furan-2,5-dicarboxaldehyde by catalytic systems based on vanadyl phosphate", Applied Catalysis A: General, vol. 289, 2005 (Available online Jun. 20, 2005), pp. 197-204.

(Continued)

*Primary Examiner* — Erich A Leeser
(74) *Attorney, Agent, or Firm* — Birch, Stewart, Kolasch & Birch, LLP

(57) ABSTRACT

Method for preparing 2,5-furan dicarboxylic acid is provided, which includes contacting a furan composition with an oxidant in the presence of a catalyst system. The furan composition includes a first compound and a second compound. The first compound is a compound of Formula 1:

(Formula 1)

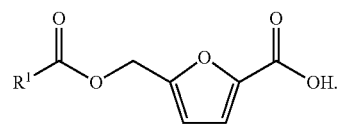

In Formula 1, $R^1$ is $C_{1-9}$ alkyl group. The second compound is a compound of Formula 2, a compound of formula 3, a compound of Formula 4, a compound of Formula 5, or combinations thereof.

(Formula 2)

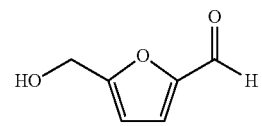

(Formula 3)

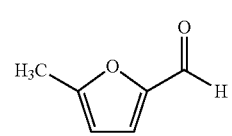

(Formula 4)

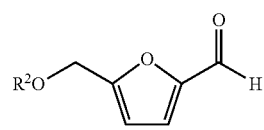

(Formula 5)

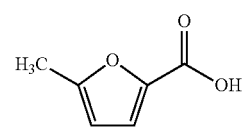

In Formula 3, $R^2$ is $C_{1-9}$ alkyl group. The 2,5-furan dicarboxylic acid is a compound of Formula 6.

(Formula 6)

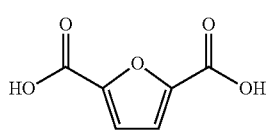

16 Claims, No Drawings

(56) References Cited

U.S. PATENT DOCUMENTS

| | | | |
|---|---|---|---|
| 2008/0103340 | A1 | 5/2008 | Binder et al. |
| 2009/0124829 | A1 | 5/2009 | Gong |
| 2009/0249395 | A1 | 10/2009 | Seidel et al. |
| 2010/0239509 | A1 | 9/2010 | Chodorowski-Kimmes et al. |
| 2010/0272660 | A1 | 10/2010 | Malle |
| 2011/0086395 | A1 | 4/2011 | Koopman et al. |
| 2011/0092720 | A1 | 4/2011 | Yutaka et al. |
| 2012/0271060 | A1 | 10/2012 | Muñoz De Diego et al. |
| 2012/0283452 | A1 | 11/2012 | Muñoz De Diego et al. |
| 2012/0302771 | A1 | 11/2012 | Janka et al. |
| 2012/0309918 | A1 | 12/2012 | Ruijssenaars et al. |
| 2013/0022771 | A1 | 1/2013 | Malet et al. |
| 2013/0137882 | A1 | 5/2013 | Borsotti et al. |

FOREIGN PATENT DOCUMENTS

| | | | |
|---|---|---|---|
| JP | 2008-88134 | A | 4/2008 |
| JP | 2009-242312 | A | 10/2009 |
| TW | 200930798 | A | 7/2009 |
| TW | 201000476 | A1 | 1/2010 |
| TW | 201137065 | A1 | 11/2011 |
| TW | 201202212 | A1 | 1/2012 |
| TW | 201209074 | A1 | 3/2012 |
| TW | 201307377 | A1 | 2/2013 |
| WO | WO 01/72732 | A2 | 10/2001 |
| WO | WO 2009/076627 | A2 | 6/2009 |
| WO | WO 2010/132740 | A2 | 11/2010 |
| WO | WO 2011/043660 | A2 | 4/2011 |
| WO | WO 2011/043661 | A1 | 4/2011 |
| WO | WO 2013/033058 | A1 | 3/2013 |
| WO | WO 2013/033081 | A2 | 3/2013 |
| WO | WO 2015/056270 | * | 4/2015 ............ C07D 307/68 |

OTHER PUBLICATIONS

Casanova et al., "Biomass into Chemicals: Aerobic Oxidation of 5-Hydroxy-methyl-2-furfural into 2,5-Furandicarboxylic Acid with Gold Nanoparticle Catalysts", ChemSusChem, vol. 2, 2009, pp. 1138-1144.

Casanova et al., "Chemicals from Biomass: Aerobic Oxidation of 5-Hydroxymethyl-2-Furaldehyde into Diformylfurane Catalyzed by Immobilized Vanadyl-Pyridine Complexes on Polymeric and Organofunctionalized Mesoporous Supports", Top Catal, vol. 52, 2009, pp. 304-314.

Gorbanev et al., "Gold-Catalyzed Aerobic Oxidation of 5-Hydroxymethyl-furfural in Water at Ambient Temperature", ChemSusChem, vol. 2, 2009, pp. 672-675.

Gupta et al., "Hydrotalcite-supported gold-nanoparticle-catalyzed highly efficient base-free aqeos oxidation of 5-hydroxymethylfurfural into 2,5-furandicarboxylic acid under atmospheric oxygen pressure", Green Chemistry, vol. 13, 2011, pp. 824-827.

Kröger et al., "A new approach for the production of 2,5-furandicarboxylic acid by in situ oxidation of 5-hydroxymethylfurfural starting from fructose", Topics in Catalysis, vol. 13, 2000, pp. 237-242.

Partenheimer et al., "Synthesis of 2,5-Diformylfuran and Furan-2,5-Dicarboxylic Acid by Catalytic Air-Oxidation of 5-Hydroxymethylfurfural. Unexpectedly Selective Aerobic Oxidation of Benzyl Alcohol to Benzaldehyde with Metal/Bromide Catalysts", Adv. Synth. Catal., vol. 343, No. 1, 2001, pp. 102-111.

Ribeiro et al., "Cooperative effect of cobalt acetylacetonate and silica in the catalytic cyclization and oxidation of fructose to 2,5-furandicarboxylic acid", Catalysis Communications, vol. 4, 2003, pp. 83-86.

Taarning et al., "Chemicals from Renewables: Aerobic Oxidation of Furfural and Hydroxymethylfurfural over Gold Catalysts", ChemSusChem, vol. 1, 2008, pp. 75-78.

Tawainese Office Action and Search Report dated Jul. 22, 2014, for Tawainese Application No. 102148617.

Tawainese Office Action and Search Report dated Mar. 11, 2015, for Tawainese Application No. 103144011.

Verdeguer et al., "Oxydation catalytique du HMF en acide 2.5-furane dicarboxyligue", Journal of Molecular Catalysis, vol. 85, 1993, pp. 327-344.

Vinke et al., "Platinum Catalyzed Oxidation of 5-Hydroxymethylfurfural", New Developments in Selective Oxidation, 1990, pp. 147-158.

* cited by examiner

METHOD FOR PREPARING 2,5-FURAN DICARBOXYLIC ACID

TECHNICAL FIELD

The technical field relates to an oxidation process of forming 2,5-furan dicarboxylic acid, and in particularly relates to starting materials thereof.

BACKGROUND 2,5-furan dicarboxylic acid (FDCA) and derivatives thereof are biomass materials formed by oxidizing 5-hydroxymethylfurfural (HMF), which is formed by dehydrating C6 fructose or glucose. FDCA is a diacid compound served as a diacid monomer of polyester. The FDCA can be esterificated and polymerized with a diol to form a series of polyester compounds. Because the FDCA has a structure similar to the commonly used terephthalic acid, it can be applied in the polyester industry and with elastomer materials. The FDCA has a furan five-membered ring and individual properties, which may form special polyesters in the polyester field to be applied in IC industry or other novel fields. The HMF have three easily oxidized functional groups such as aldehyde group, hydroxyl group, and furan ring, such that the diacid products of high yield formed by oxidizing the HMF must be performed through an oxidation process with high selectivity. Most of conventional research focused on various new catalyst type to enhance the yield and selectivity of the FDCA product. However, changing the new catalyst system often greatly increases the equipment cost, and cannot be immediately applied in the industry.

Accordingly, a method of increasing the yield and selectivity of the FDCA product through existing catalyst systems is called for.

SUMMARY

One embodiment of the disclosure provides a method for preparing 2,5-furan dicarboxylic acid, including: contacting a furan composition with an oxidant in the presence of a catalyst system, wherein the furan composition includes a first compound and a second compound, the first compound is a compound of Formula 1:

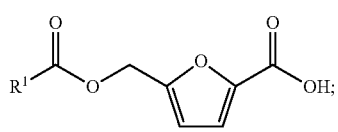

(Formula 1)

wherein $R^1$ is $C_{1-9}$ alkyl group, wherein the second compound is a compound of Formula 2, a compound of formula 3, a compound of Formula 4, a compound of Formula 5, or a combination thereof;

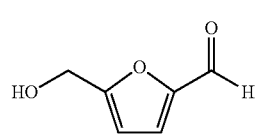

(Formula 2)

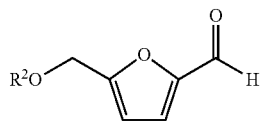

(Formula 3)

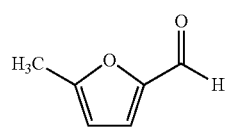

(Formula 4)

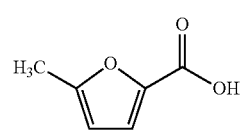

(Formula 5)

wherein $R^2$ is $C^{1-9}$ alkyl group.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details.

The disclosure provides a method for preparing 2,5-furan dicarboxylic acid, comprising: contacting a furan composition with an oxidant in the presence of a catalyst system, wherein the furan composition includes a first compound and a second compound. The furan composition includes a first compound and a second compound. The first compound is a compound of Formula 1:

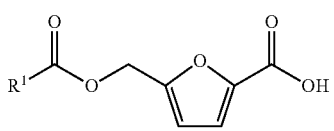

(Formula 1)

In Formula 1, $R^1$ is $C_{1-9}$ alkyl group. In one embodiment, $R^1$ is methyl group or ethyl group. The second compound is a compound of Formula 2, a compound of formula 3, a compound of Formula 4, a compound of Formula 5, or a combination thereof.

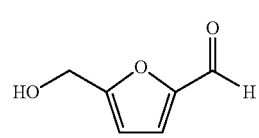

(Formula 2)

(Formula 3)

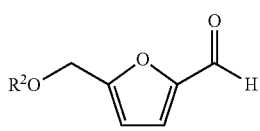

(Formula 4)

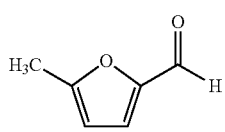

(Formula 5)

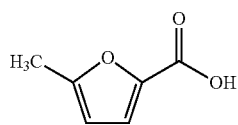

In Formula 3, $R^2$ is $C_{1-9}$ alkyl group. In one embodiment, $R^2$ is ethyl group. In one embodiment, the furan composition is a combination of the compound of Formula 1 and the compound of Formula 2. In one embodiment, the furan composition is a combination of the compound of Formula 1 and the compound of Formula 3. In one embodiment, the furan composition is a combination of the compound of Formula 1 and the compound of Formula 4.

The furan composition is oxidized by the oxidant with the catalyst system to form the 2,5-furan dicarboxylic acid (FDCA) as shown in Formula 6.

(Formula 6)

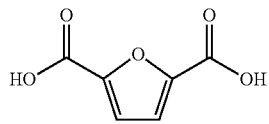

In one embodiment, the aldehyde group in the compound of Formula 2 can be selectively oxidized to a carboxylic acid group, and the alcohol group in the compound of Formula 2 can be esterified with a carboxylic acid or an acid anhydride of different carbon numbers, thereby forming the compound of Formula 1. The above reactions are shown in Formula 7.

(Formula 7)

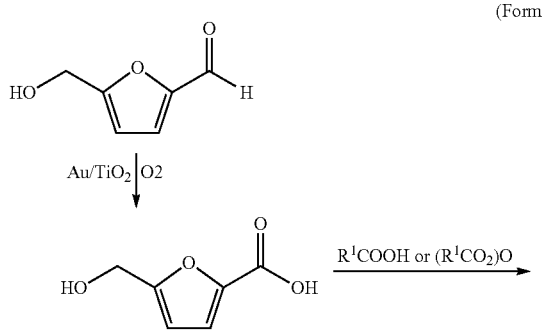

-continued

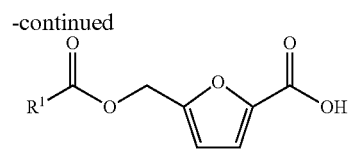

In one embodiment, the oxidant includes oxygen. For example, the atmosphere air (with 20 vol % oxygen) may serve as the oxidant. In one embodiment, the catalyst system includes at least one selected from the group consisting of Co(II), Mn(II), Ce(II), a salt thereof, and a combination thereof. For example, the salt may have an anion selected from the group consisting of an acetate, acetate hydrate, bromide, chloride, fluoride, iodide, alkoxide, azide, oxalate, carbonate, carboxylate, hydroxide, nitrate, borate, oxide, acetylacetonate, or a combination thereof In one embodiment, the catalyst system includes a source of bromine (such as bromide). For example, the catalyst system includes Co(II), Mn(II), and bromide. Alternatively, the catalyst system includes Ce(II), Mn(II), and bromide. In one embodiment, the catalyst system comprises at least one additional metal, such as zirconium, hafnium, copper, nickel, zinc, or a combination thereof. For example, the additional metal is zirconium.

For example, cobalt acetate ($Co(OAc)_2.4H_2O$), manganese acetate ($Mn(OAc)_2.4H_2O$), and sodium bromide may serve as the catalyst system. In one embodiment, the furan composition is oxidized by the catalyst system and the oxidant under a pressure of 8 bar to 60 bar and at a temperature of 100° C. to 250° C. Alternatively, the oxidation is performed under a pressure of 10 bar to 25 bar and at a temperature of 130° C. to 220° C. An overly high oxidation temperature easily polymerizes the raw materials (e.g. HMF) or cracks the product, thereby reducing product yield. An overly low oxidation pressure and/or an overly low temperature may slow the reaction rate and lower the 2,5-furan dicarboxylic acid product yield. As proven in experiments, the combination of the first compound and the second compound in the oxidation process has a higher FDCA selectivity and a higher FDCA yield.

In one embodiment, the first compound (5-(acetoxymethyl)-2-furoic acid) and the second compound (5-hydroxymethylfurfural) have a weight ratio of 1:1000000 to 1:0.5. In one embodiment, the first compound (5-(acetoxymethyl)-2-furoic acid) and the second compound (5-hydroxymethylfurfural) have a weight ratio of 1:100000 to 1:1.5. An overly low ratio of the first compound cannot efficiently enhance the FDCA selectivity and the FDCA yield.

In one embodiment, the weight ratio of catalyst/(reactants without catalyst+solvent) is between 0.05 wt % to 8 wt %. Alternatively, the weight ratio of catalyst/(reactants without catalyst+solvent) is between 0.1 wt % to 6 wt %. The oxidation cannot be performed well with an overly low ratio of the catalyst. An overly high ratio of the catalyst may enhance the oxidation cost.

The above oxidation process can be performed as a one-pot type or a semibatch type. For example, the one-pot type involves mixing the reactants and the catalyst in a reactor, then increasing the pressure and the temperature of the reactor, and then introducing gas into the reactor for the oxidation process. In the batch type, the pressure and temperature of the reactor with a catalyst solution therein are increased, and gas is introduced into the reactor. Subsequently, the reactants are slowly fed into the catalyst solution to perform the oxidation process. In a continuous type, the pressure and temperature of the reactor with a catalyst solution therein are increased, and gas is introduced into the reactor. Subsequently, the reactants are slowly fed into the catalyst solution to perform the oxidation process. Simultaneously, the product in the reactor is output with an appropriate rate from the reactor to a purification element. The one-pot type, the semibatch type, and the continuous type can be combined as a multi-stage reactor system.

Below, exemplary embodiments will be described in detail so as to be easily realized by a person having ordinary knowledge in the art. The inventive concept may be embodied in various forms without being limited to the exemplary embodiments set forth herein. Descriptions of well-known parts are omitted for clarity.

EXAMPLES

Preparation Example 1

Preparation of 5-hydroxymethyl-2-furoic acid (HMFCA)

10 g of HMF, 150 g of water, and 1 g of catalyst (4% Au/TiO2) were added into a round bottom bottle (250 mL) and then heated to 70° C. Air under atmosphere pressure was introduced into the liquid in the flask. The pH value of the above reaction was controlled to 10 by adding a sodium hydroxide aqueous solution into the flask. The reaction was continued for 7 hours to obtain a crude aqueous solution. The crude aqueous solution was extracted by 200 mL of ethyl acetate two times, and the aqueous phase of the extractions was collected by a separatory funnel. The collected aqueous phase was titrated by concentrated hydrochloric acid (HCl) until its pH value reached 3. The acidified aqueous phase was extracted by 200 mL of ethyl acetate two times, and the organic phase of the extractions was collected. The collected organic phase was vacuumed concentrated to obtain 2.74 g of solid, which was 5-hydroxymethyl-2-furoic acid (HMFCA). The above reaction is shown in Formula 8. The product of Formula 8 had NMR spectra as below: $^1$H NMR (400 MHz, d-DMSO): 13.08 (br, 1H), 7.14 (d, 1H, J=3.4 Hz), 6.45 (d, 1H, J=3.4 Hz), 5.59 (s, 1H), 4.44 (s, 2H); $^{13}$C NMR (100 M Hz, d-DMSO): 160.1, 159.8, 144.4, 119.0, 109.4, 56.2.

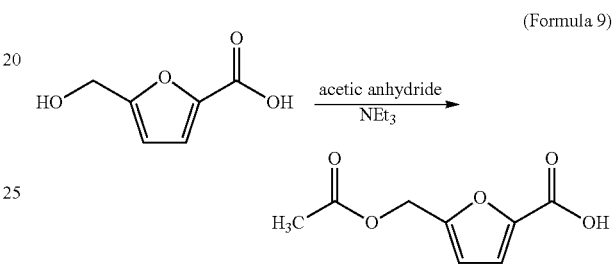

(Formula 8)

Preparation Example 2

Preparation of 5-(acetoxymethyl)-2-furoic acid 15.64 g of HMFCA (104 mmol), 300 mL of ethyl ether, and 20.24 g of triethylamine (NEt$_3$, 0.2 mol) were added into a twin neck bottle (250 mL) and stirred to be completely dissolved. 11.78 mL of acetic anhydride (124.8 mmol) was then slowly added into the twin neck bottle in an ice bath, and the ice bath was then removed after the addition of acetic anhydride for slowly warming up the reaction to room temperature. The reaction was continued at room temperature for 14 hours, and 3M HCl was then added into the twin neck bottle to acidify the solution in the twin neck bottle. The acidified solution was extracted by de-ionized water three times, and the organic phase of the extractions was collected and then dried by anhydrous MgSO$_4$. The organic phase was concentrated to obtain a yellow solid. The yellow solid was washed by n-hexane and then dried to obtain 17.84 g of 5-(acetoxymethyl)-2-furoic acid product (yield=93%), as shown in Formula 1 with R$^1$ being methyl group. The above reaction is shown in Formula 9. The product of Formula 9 had NMR spectra as below: $^1$H NMR (400 M Hz, CDCl$_3$): 7.23 (d, 1H, J=3.5 Hz), 6.51 (d, 1H, J=3.5 Hz), 5.07 (s, 2H), 2.07 (s, 3H). $^{13}$C NMR (100 M Hz, CDCl$_3$): 170.6, 162.5, 154.4, 144.0, 120.5, 112.5, 57.8, 20.7. The product of Formula 9 had mass spectrum as below: HRMS (EI, m/z): calcd. for C$_8$H$_8$O$_5$ 184.15. found 184.11 (M$^+$).

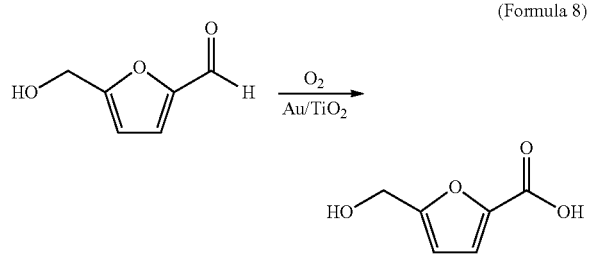

(Formula 9)

Preparation Example 3

Preparation of 5-(propionyloxy methyl)-2-furoic acid 9.70 g of HMFCA (69 mmol), 100 mL of dichloromethane, and 10.47 g of triethylamine (NEt$_3$, 0.1 mol) were added into a twin neck bottle (200 mL) and stirred to be completely dissolved. 10.78 g of propionic anhydride (82.8 mmol) was then slowly added into the twin neck bottle in an ice bath, and the ice bath was then removed after the addition of propionic anhydride for slowly warming up the reaction to room temperature. The reaction was continued at room temperature for 16 hours, and 3M HCl was then added into the twin neck bottle to acidify the solution in the twin neck bottle. The acidified solution was extracted by de-ionized water three times, and the organic phase of the extractions was collected. The organic phase was vacuumed concentrated at 80° C. and then put into a refrigerator overnight to obtain a yellow solid. The yellow solid was washed by n-hexane and then dried to obtain 10.38 g of 5-(propionyloxymethyl)-2-furoic acid product (yield=76%), as shown in Formula 1 with R$^1$ being ethyl group. The above reaction is shown in Formula 10. The product of Formula 10 had NMR spectra as below: $^1$H NMR (400 M Hz, CDCl$_3$): 7.25 (d, 1H, J=3.4 Hz), 6.52 (d, 1H, J=3.4 Hz), 5.09 (s, 2H), 2.35 (q, 2H, J=7.6 Hz), 1.14 (t, 3H, J=7.6 Hz). $^{13}$C NMR (100 M Hz, CDCl$_3$): 174.0, 162.9, 154.6, 143.9, 120.6, 112.3, 57.7, 27.2, 8.8. The product of Formula 9 had mass spectrum as below: HRMS (EI, m/z): calcd. for C$_9$H$_{10}$O$_5$ 198.17. found 198.12 (M$^+$).

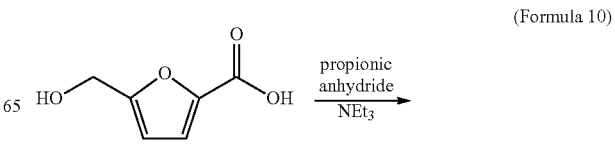

(Formula 10)

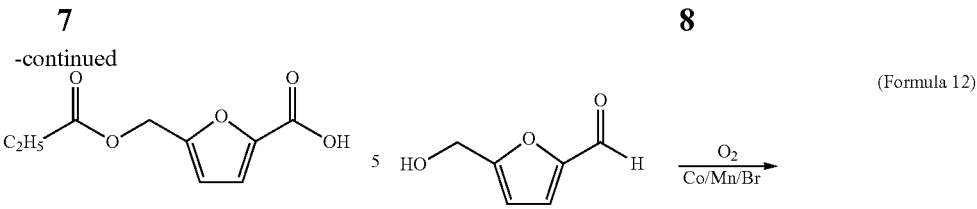

Comparative Example 1-1

4.74 g of cobalt acetate (Co(OAc)$_2$.4H$_2$O), 2.33 g of manganese acetate (Mn(OAc)$_2$.4H$_2$O), 0.49 g of sodium bromide, 190 g of acetic anhydride, and 10 g of de-ionized water were added into a high pressure autoclave reactor, and then stirred to be evenly mixed for completely dissolving the catalyst. 3.24 g of 5-(propionyloxymethyl)-2-furoic acid (Formula 1 with R$^1$ being ethyl group) was then added into the high pressure autoclave reactor. The high pressure autoclave reactor was then sealed with a pressure increased to 20 bar. The mixture in the autoclave reactor was stirred at a rate of 300 rpm and then heated to 130° C. Atmosphere air was then introduced into the mixture at 130° C. for 1 hour, and the mixture was heated to 150° C. and remained at 150° C. for 3 hours. Thereafter, the autoclave reactor was cooled, and pressure in the autoclave was then released. The crude in the autoclave reactor was analyzed by liquid chromatography to determine the conversion rate of 5-(propionyloxymethyl)-2-furoic acid being 99.33%, and the yield of the FDCA (Formula 6) being 52.01%. The above reaction is shown as Formula (Formula 11)

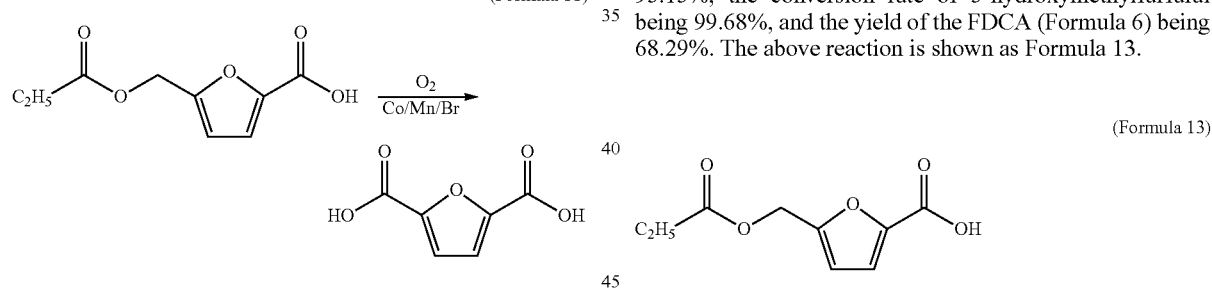

Comparative Example 1-2

0.59 g of cobalt acetate (Co(OAc)$_2$.4H$_2$O), 0.58 g of manganese acetate (Mn(OAc)$_2$.4H$_2$O), 0.13 g of sodium bromide, 190 g of acetic anhydride, and 10 g of de-ionized water were added into a high pressure autoclave reactor, and then stirred to be evenly mixed for completely dissolving the catalyst. 10 g of 5-hydroxymethylfurfural (Formula 2) was then added into the high pressure autoclave reactor. The high pressure autoclave reactor was then sealed with a pressure increased to 20 bar. The mixture in the autoclave reactor was stirred at a rate of 300 rpm and then heated to 130° C. Atmosphere air was then introduced into the mixture at 130° C. for 1 hour, and the mixture was heated to 150° C. and remained at 150° C. for 3 hours. Thereafter, the autoclave reactor was cooled, and pressure in the autoclave was then released. The crude in the autoclave reactor was analyzed by liquid chromatography to determine the conversion rate of 5-hydroxymethylfurfural being 99.80%, and the yield of the FDCA (Formula 6) being 60.07%. The above reaction is shown as Formula 12.

(Formula 12)

Example 1-1

0.59 g of cobalt acetate (Co(OAc)$_2$.4H$_2$O), 0.58 g of manganese acetate (Mn(OAc)$_2$.4H$_2$O), 0.13 g of sodium bromide, 190 g of acetic anhydride, and 10 g of de-ionized water were added into a high pressure autoclave reactor, and then stirred to be evenly mixed for completely dissolving the catalyst. 3.24 g of 5-(propionyloxymethyl)-2-furoic acid (Formula 1 with R$^1$ being ethyl group) and 5 g of 5-hydroxymethylfurfural (Formula 2) was then added into the high pressure autoclave reactor. The high pressure autoclave reactor was then sealed with a pressure increased to 20 bar. The mixture in the autoclave reactor was stirred at a rate of 300 rpm and then heated to 130° C. Atmosphere air was then introduced into the mixture at 130° C. for 1 hour, and the mixture was heated to 150° C. and remained at 150° C. for 3 hours. Thereafter, the autoclave reactor was cooled, and pressure in the autoclave was then released. The crude in the autoclave reactor was analyzed by liquid chromatography to determine the conversion rate of 5-(propionyloxymethyl)-2-furoic acid being 95.15%, the conversion rate of 5-hydroxymethylfurfural being 99.68%, and the yield of the FDCA (Formula 6) being 68.29%. The above reaction is shown as Formula 13.

(Formula 13)

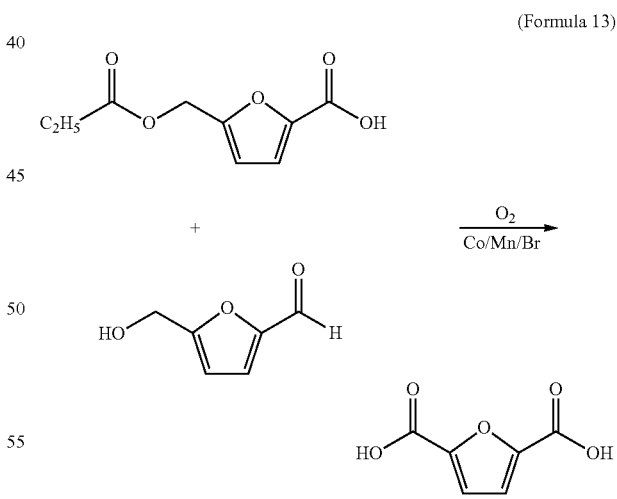

Example 1-2

0.59 g of cobalt acetate (Co(OAc)$_2$.4H$_2$O), 0.58 g of manganese acetate (Mn(OAc)$_2$.4H$_2$O), 0.13 g of sodium bromide, 190 g of acetic anhydride, and 10 g of de-ionized water were added into a high pressure autoclave reactor, and then stirred to be evenly mixed for completely dissolving the catalyst. 0.1 g of 5-(propionyloxymethyl)-2-furoic acid (Formula 1 with $R^1$ being ethyl group) and 8.4 g of 5-hydroxymethylfurfural (Formula 2) was then added into the high pressure autoclave reactor. The high pressure autoclave reactor was then sealed with a pressure increased to 20 bar. The mixture in the autoclave reactor was stirred at a rate of 300 rpm and then heated to 130° C. Atmosphere air was then introduced into the mixture at 130° C. for 1 hour, and the mixture was heated to 150° C. and remained at 150° C. for 3 hours. Thereafter, the autoclave reactor was cooled, and pressure in the autoclave was then released. The crude in the autoclave reactor was analyzed by liquid chromatography to determine the conversion rate of 5-(propionyloxymethyl)-2-furoic acid being 94.12%, the conversion rate of 5-hydroxymethylfurfural being 99.80%, and the yield of the FDCA (Formula 6) being 65.82%. The above reaction is shown as Formula 13.

Example 1-3

4.74 g of cobalt acetate ($Co(OAc)_2.4H_2O$), 2.33 g of manganese acetate ($Mn(OAc)_2.4H_2O$), 0.49 g of sodium bromide, and 100 g of 95% acetic acid (containing 5% water) were added into a high pressure autoclave reactor, and then stirred to be evenly mixed for completely dissolving the catalyst. The high pressure autoclave reactor was then sealed with a pressure increased to 20 bar by filling nitrogen. The mixture in the autoclave reactor was stirred at a rate of 300 rpm and then heated to 150° C. Atmosphere air was then introduced into the mixture at 150° C. 0.11 g of 5-(propionyloxymethyl)-2-furoic acid (Formula 1 with $R^1$ being ethyl group), 20 g of 5-hydroxymethylfurfural (Formula 2), and 100 g of 95% acetic acid were evenly mixed to form a solution, and then gradually added into the high pressure autoclave reactor through a feeding pump to be reacted. The reaction was remained at 150° C. for 5 hours. Thereafter, the autoclave reactor was cooled, and pressure in the autoclave was then released. The crude in the autoclave reactor was analyzed by liquid chromatography to determine the conversion rate of 5-(propionyloxymethyl)-2-furoic acid being 96.86%, the conversion rate of 5-hydroxymethylfurfural being 99.91%, and the yield of the FDCA (Formula 6) being 67.12%. The above reaction is shown as Formula 13.

Example 1-4

7.11 g of cobalt acetate ($Co(OAc)_2.4H_2O$), 3.50 g of manganese acetate ($Mn(OAc)_2.4H_2O$), 0.74 g of sodium bromide, and 100 g of 95% acetic acid (containing 5% water) were added into a high pressure autoclave reactor, and then stirred to be evenly mixed for completely dissolving the catalyst. The high pressure autoclave reactor was then sealed with a pressure increased to 20 bar by filling nitrogen. The mixture in the autoclave reactor was stirred at a rate of 300 rpm and then heated to 150° C. Atmosphere air was then introduced into the mixture at 150° C. 3.2 g of 5-(propionyloxymethyl)-2-furoic acid (Formula 1 with $R^1$ being ethyl group), 35 g of 5-hydroxymethylfurfural (Formula 2), and 65 g of 95% acetic acid were evenly mixed to form a solution, and then gradually added into the high pressure autoclave reactor through a feeding pump to be reacted. The reaction was remained at 150° C. for 11 hour. Thereafter, the autoclave reactor was cooled, and pressure in the autoclave was then released. The crude in the autoclave reactor was analyzed by liquid chromatography to determine the conversion rate of 5-(propionyloxymethyl)-2-furoic acid being 99.74%, the conversion rate of 5-hydroxymethylfurfural being 99.89%, and the yield of the FDCA (Formula 6) being 75.02%. The above reaction is shown as Formula 13.

Example 1-5

1.77 g of cobalt acetate ($Co(OAc)_2.4H_2O$), 0.87 g of manganese acetate ($Mn(OAc)_2.4H_2O$), 0.74 g of sodium bromide, and 100 g of 95% acetic acid (containing 5% water) were added into a high pressure autoclave reactor, and then stirred to be evenly mixed for completely dissolving the catalyst. The high pressure autoclave reactor was then sealed with a pressure increased to 20 bar by filling nitrogen. The mixture in the autoclave reactor was stirred at a rate of 300 rpm and then heated to 150° C. Atmosphere air was then introduced into the mixture at 150° C. 0.01 g of 5-(propionyloxymethyl)-2-furoic acid (Formula 1 with $R^1$ being ethyl group), 35 g of 5-hydroxymethylfurfural (Formula 2), and 65 g of 95% acetic acid were evenly mixed to form a solution, and then gradually added into the high pressure autoclave reactor through a feeding pump to be reacted. The reaction was remained at 150° C. for 11 hour. Thereafter, the autoclave reactor was cooled, and pressure in the autoclave was then released. The crude in the autoclave reactor was analyzed by liquid chromatography to determine the conversion rate of 5-(propionyloxymethyl)-2-furoic acid being 96.37%, the conversion rate of 5-hydroxymethylfurfural being 97.58%, and the yield of the FDCA (Formula 6) being 64.57%. The above reaction is shown as Formula 13.

Example 1-6

1.77 g of cobalt acetate ($Co(OAc)_2.4H_2O$), 0.87 g of manganese acetate ($Mn(OAc)_2.4H_2O$), 0.74 g of sodium bromide, 0.1 g of tetrakis(2,4-pentanedionato-o,o')-zirconium, and 100 g of 95% acetic acid (containing 5% water) were added into a high pressure autoclave reactor, and then stirred to be evenly mixed for completely dissolving the catalyst. The high pressure autoclave reactor was then sealed with a pressure increased to 20 bar by filling nitrogen. The mixture in the autoclave reactor was stirred at a rate of 300 rpm and then heated to 150° C. Oxygen/nitrogen (5%/95%) was then introduced into the mixture at 150° C. 0.001 g of 5-(propionyloxymethyl)-2-furoic acid (Formula 1 with $R^1$ being ethyl group), 40 g of 5-hydroxymethylfurfural (Formula 2), and 60 g of 95% acetic acid were evenly mixed to form a solution, and then gradually added into the high pressure autoclave reactor through a feeding pump to be reacted. The reaction was remained at 150° C. for 11 hour. Thereafter, the autoclave reactor was cooled, and pressure in the autoclave was then released. The crude in the autoclave reactor was analyzed by liquid chromatography to determine the conversion rate of 5-(propionyloxymethyl)-2-furoic acid being 80.44%, the conversion rate of 5-hydroxymethylfurfural being 85.73%, and the yield of the FDCA (Formula 6) being 30.07%. The above reaction is shown as Formula 13.

Example 1-7

7.11 g of cobalt acetate ($Co(OAc)_2.4H_2O$), 3.5 g of manganese acetate ($Mn(OAc)_2.4H_2O$), 0.74 g of sodium bromide, and 100 g of 95% acetic acid (containing 5% water) were added into a high pressure autoclave reactor, and then stirred to be evenly mixed for completely dissolving the catalyst. The high pressure autoclave reactor was then sealed with a pressure increased to 20 bar by filling nitrogen. The mixture in the autoclave reactor was stirred at a rate of 300 rpm and then heated to 150° C. Oxygen/nitrogen (5%/95%) was then introduced into the mixture at 150° C. 0.23 g of 5-(acetoxymethyl)-2-furoic acid (Formula 1 with $R^1$ being methyl group), 30 g of 5-hydroxymethylfurfural (Formula 2), and 100 g of 95% acetic acid were evenly mixed to form a solution, and then gradually added into the high pressure autoclave reactor through a feeding pump to be reacted. The reaction was remained at 150° C. for 4 hours, and then heated to 170° C. and remained at 170° C. for 2 hours. Thereafter, the autoclave reactor was cooled, and pressure in the autoclave was then released. The crude in the autoclave reactor was analyzed by liquid chromatography to determine the conversion rate of 5-(acetoxymethyl)-2-furoic acid being 89.79%, the conversion rate of 5-hydroxymethylfurfural being 98.34%, and the yield of the FDCA (Formula 6) being 32.39%. The above reaction is shown as Formula 14.

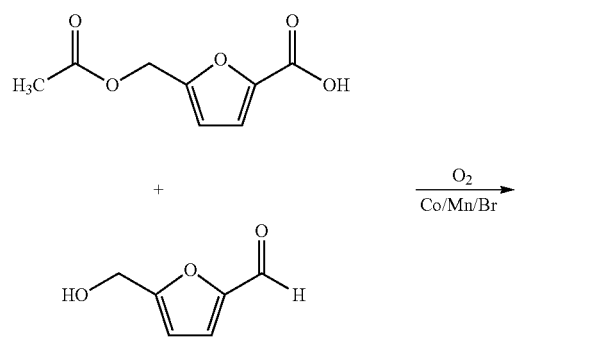

(Formula 14)

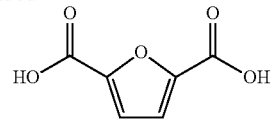

Example 1-8

7.11 g of cobalt acetate ($Co(OAc)_2 \cdot 4H_2O$), 3.5 g of manganese acetate ($Mn(OAc)_2 \cdot 4H_2O$), 0.74 g of sodium bromide, and 100 g of 95% acetic acid (containing 5% water) were added into a high pressure autoclave reactor, and then stirred to be evenly mixed for completely dissolving the catalyst. The high pressure autoclave reactor was then sealed with a pressure increased to 25 bar by filling nitrogen. The mixture in the autoclave reactor was stirred at a rate of 300 rpm and then heated to 150° C. Atmosphere air was then introduced into the mixture at 150° C. 2.3 g of 5-(acetoxymethyl)-2-furoic acid (Formula 1 with $R^1$ being methyl group), 30 g of 5-hydroxymethylfurfural (Formula 2), and 100 g of 95% acetic acid were evenly mixed to form a solution, and then gradually added into the high pressure autoclave reactor through a feeding pump to be reacted. The reaction was remained at 150° C. for 11 hour. Thereafter, the autoclave reactor was cooled, and pressure in the autoclave was then released. The crude in the autoclave reactor was analyzed by liquid chromatography to determine the conversion rate of 5-(acetoxymethyl)-2-furoic acid being 99.66%, the conversion rate of 5-hydroxymethylfurfural being 99.87%, and the yield of the FDCA (Formula 6) being 74.66%. The above reaction is shown as Formula 14.

TABLE 1

| | Reactants | Co/Mn/Br catalyst | Reaction temperature (° C.) | Reaction pressure (bar) | Reactant conversion rate (%) | FDCA selectivity (mole %) | FDCA yield |
|---|---|---|---|---|---|---|---|
| Comparative Example 1-1 | 5-(propionyloxy methyl)-2-furoic acid (1.6 wt %) | 3.72 wt % | 130° C. (1 h) + 150° C. (3 h) | 20 | 5-(propionyloxymethyl)-2-furoic acid = 99.33 | 52.36 | 52.01 |
| Comparative Example 1-2 | 5-hydroxymethyl furfural (4.8 wt %) | 0.62 wt % | 130° C. (1 h) + 150° C. (3 h) | 20 | 5-hydroxymethylfurfural = 99.80 | 60.19 | 60.07 |
| Example 1-1 | 5-hydroxymethyl furfural (2.4 wt %) and 5-(propionyloxy methyl)-2-furoic acid (1.6 wt %) | 0.62 wt % | 130° C. (1 h) + 150° C. (3 h) | 20 | 5-hydroxymethylfurfural = 99.68, 5-(propionyloxy methyl)-2-furoic acid = 95.15 | 69.44 | 68.29 |
| Example 1-2 | 5-hydroxymethyl furfural (4.0 wt %) and 5-(propionyloxy methyl)-2-furoic acid (0.048 wt %) | 0.62 wt % | 130° C. (1 h) + 150° C. (3 h) | 20 | 5-hydroxymethylfurfural = 99.80, 5-(propionyloxy methyl)-2-furoic acid = 94.12 | 65.98 | 65.82 |
| Example 1-3 | 5-hydroxymethyl furfural (9 wt %) and 5-(propionyloxy methyl)-2-furoic acid (0.05 wt %) | 3.43 wt % | 150° C. (5 h) | 20 | 5-hydroxymethylfurfural = 99.91, 5-(propionyloxy methyl)-2-furoic acid = 96.86 | 67.18 | 67.12 |
| Example 1-4 | 5-hydroxymethyl furfural (17.2 wt %) and 5-(propionyloxy methyl)-2-furoic acid (1.6 wt %) | 5.59 wt % | 150° C. (11 h) | 20 | 5-hydroxymethylfurfural = 99.89, 5-(propionyloxy methyl)-2-furoic acid = 99.74 | 75.11 | 75.02 |
| Example 1-5 | 5-hydroxymethyl furfural (17.5 wt %) and 5-(propionyloxy methyl)-2-furoic acid (0.005 wt %) | 1.69 wt % | 150° C. (11 h) | 20 | 5-hydroxymethylfurfural = 97.58, 5-(propionyloxy methyl)-2-furoic acid = 96.37 | 66.17 | 64.57 |
| Example 1-6 | 5-hydroxymethyl furfural (20.0 wt %) and 5-(propionyloxy methyl)-2-furoic acid (0.0005 wt %) | 1.74 wt % (with further zirconium catalyst) | 150° C. (11 h) | 20 | 5-hydroxymethylfurfural = 85.73, 5-(propionyloxy methyl)-2-furoic acid = 80.44 | 35.07 | 30.07 |

TABLE 1-continued

|  | Reactants | Co/Mn/Br catalyst | Reaction temperature (° C.) | Reaction pressure (bar) | Reactant conversion rate (%) | FDCA selectivity (mole %) | FDCA yield |
|---|---|---|---|---|---|---|---|
| Example 1-7 | 5-hydroxymethyl furfural (13.0 wt %) and 5-(acetoxy methyl)-2-furoic acid (0.1 wt %) | 4.93 wt % | 150° C. (4 h) + 170° C. (2 h) | 20 | 5-hydroxymethylfurfural = 98.34, 5-(acetoxy methyl)-2-furoic acid = 89.79 | 32.95 | 32.39 |
| Example 1-8 | 5-hydroxymethyl furfural (13.0 wt %) and 5-(acetoxy methyl)-2-furoic acid (1 wt %) | 4.89 wt % | 150° C. (11 h) | 25 | 5-hydroxymethylfurfural = 99.87, 5-(acetoxy methyl)-2-furoic acid = 99.66 | 74.77 | 74.66 |

Note 1: In Comparative Examples 1-1 and 1-2 and Examples 1-1 to 1-5 and 1-8, atmosphere air was introduced into the mixture. In Examples 1-6 and 1-7, oxygen/nitrogen (5%/95%) was introduced into the mixture.

Note 2: The catalyst was Co—Mn—Br in Comparative Examples 1-1 and 1-2 and Examples 1-1 to 1-4 and 1-6 to 1-8. The catalyst was Co—Mn—Br with Zr assistant catalyst (Co—Mn—Br—Zr) in Example 1-5.

Note 3: The reactant weight ratio was defined as reactants/(reactants without catalyst+solvent), and the catalyst weight ratio was defined as catalyst/(reactants without catalyst+solvent).

As comparison between Comparative Examples 1-1, Comparative Example 1-2, Example 1-1, and Example 1-2, the combination of 5-(propionyloxymethyl)-2-furoic acid and 5-hydroxymethyl furfural in the oxidation process had a higher FDCA selectivity and a higher FDCA yield.

As shown in Examples 1-5, a small amount of additional 5-(propionyloxymethyl)-2-furoic acid may efficiently enhance the FDCA selectivity and the FDCA yield.

On the other hand, Examples 1-6 and 1-7 had lower FDCA selectivity and lower FDCA yield due to oxygen/nitrogen (5%/95%, not atmosphere air) being introduced into the mixture.

Comparative Example 2

0.59 g of cobalt acetate ($Co(OAc)_2.4H_2O$), 0.58 g of manganese acetate ($Mn(OAc)_2.4H_2O$), 0.13 g of sodium bromide, 190 g of acetic anhydride, and 10 g of de-ionized water were added into a high pressure autoclave reactor, and then stirred to be evenly mixed for completely dissolving the catalyst. 5 g of 5-ethoxymethyl furfural (Formula 3 with $R^2$ being ethyl group) was then added into the high pressure autoclave reactor. The high pressure autoclave reactor was then sealed with a pressure increased to 20 bar. The mixture in the autoclave reactor was stirred at a rate of 300 rpm and then heated to 130° C. Atmosphere air was then introduced into the mixture at 130° C. for 1 hour, and the mixture was heated to 150° C. and remained at 150° C. for 3 hours. Thereafter, the autoclave reactor was cooled, and pressure in the autoclave was then released. The crude in the autoclave reactor was analyzed by liquid chromatography to determine the conversion rate of 5-ethoxymethyl furfural being 99.91%, and the yield of the FDCA (Formula 6) being 34.95%. The above reaction is shown as Formula 15.

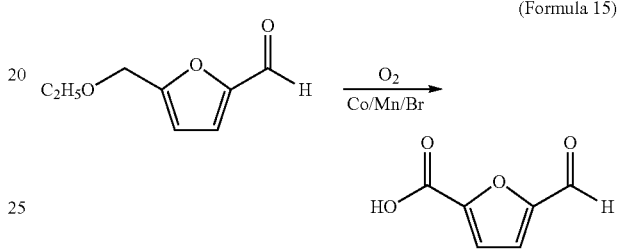

Example 2

0.59 g of cobalt acetate ($Co(OAc)_2.4H_2O$), 0.58 g of manganese acetate ($Mn(OAc)_2.4H_2O$), 0.13 g of sodium bromide, 190 g of acetic anhydride, and 10 g of de-ionized water were added into a high pressure autoclave reactor, and then stirred to be evenly mixed for completely dissolving the catalyst. 3.24 g of 5-(propionyloxymethyl)-2-furoic acid (Formula 1 with $R^1$ being ethyl group) and 5 g of 5-ethoxymethyl furfural (Formula 3 with $R^2$ being ethyl group) were then added into the high pressure autoclave reactor. The high pressure autoclave reactor was then sealed with a pressure increased to 20 bar. The mixture in the autoclave reactor was stirred at a rate of 300 rpm and then heated to 130° C. Atmosphere air was then introduced into the mixture at 130° C. for 1 hour, and the mixture was heated to 150° C. and remained at 150° C. for 3 hours. Thereafter, the autoclave reactor was cooled, and pressure in the autoclave was then released. The crude in the autoclave reactor was analyzed by liquid chromatography to determine the conversion rate of 5-(propionyloxymethyl)-2-furoic acid being 99.53%, the conversion rate of 5-ethoxymethyl furfural being 64.36%, and the yield of the FDCA (Formula 6) being 54.74%. The above reaction is shown as Formula 16.

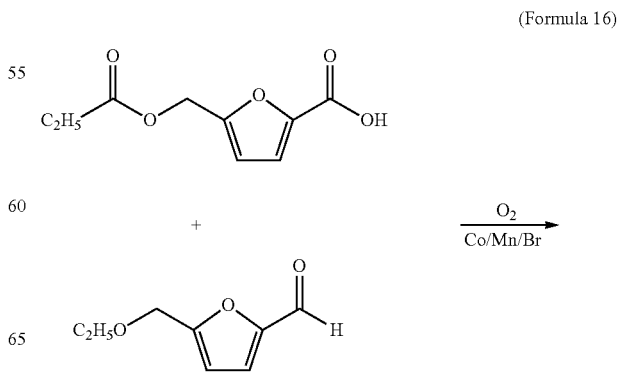

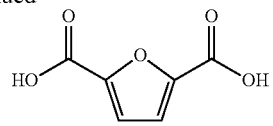

TABLE 2

| | Reactants | Co/Mn/Br Catalyst | Reaction temperature (° C.) | Reaction pressure (bar) | Reactants conversion rate (%) | FDCA selectivity (mole %) | FDCA yield (%) |
|---|---|---|---|---|---|---|---|
| Comparative Example 1-1 | 5-(propionyloxy methyl)-2-furoic acid (1.6 wt %) | 3.72 wt % | 130° C. (1 h) + 150° C. (3 h) | 20 | 5-(propionyloxy methyl)-2-furoic acid = 99.33 | 52.36 | 52.01 |
| Comparative Example 2 | 5-ethoxymethyl furfural (2.4 wt %) | 0.63 wt % | 130° C. (1 h) + 150° C. (3 h) | 20 | 5-ethoxymethyl furfural = 99.91 | 34.98 | 34.95 |
| Example 2 | 5-ethoxymethyl furfural (2.4 wt %) and 5-(propionyl oxymethyl)-2-furoic acid (1.6 wt %) | 0.62 wt % | 130° C. (1 h) + 150° C. (3 h) | 20 | 5-(propionyloxy methyl)-2-furoic acid = 99.53, 5-ethoxymethyl furfural = 64.36 | 62.39 | 54.74 |

As comparison between Comparative Examples 1-1, Comparative Example 2, and Example 2, the combination of 5-(propionyloxymethyl)-2-furoic acid and 5-ethoxymethyl furfural in the oxidation process had a higher FDCA selectivity and a higher FDCA yield.

Comparative Example 3-1

0.59 g of cobalt acetate ($Co(OAc)_2 \cdot 4H_2O$), 0.58 g of manganese acetate ($Mn(OAc)_2 \cdot 4H_2O$), 0.13 g of sodium bromide, 190 g of acetic anhydride, and 10 g of de-ionized water were added into a high pressure autoclave reactor, and then stirred to be evenly mixed for completely dissolving the catalyst. 3.24 g of 5-(acetoxymethyl)-2-furoic acid (Formula 1 with $R^1$ being methyl group) was then added into the high pressure autoclave reactor. The high pressure autoclave reactor was then sealed with a pressure increased to 20 bar. The mixture in the autoclave reactor was stirred at a rate of 300 rpm and then heated to 130° C. Atmosphere air was then introduced into the mixture at 130° C. for 1 hour, and the mixture was heated to 150° C. and remained at 150° C. for 3 hours. Thereafter, the autoclave reactor was cooled, and pressure in the autoclave was then released. The crude in the autoclave reactor was analyzed by liquid chromatography to determine the conversion rate of 5-(acetoxymethyl)-2-furoic acid being 99.36%, and the yield of the FDCA (Formula 6) being 40.50%. The above reaction is shown as Formula 17.

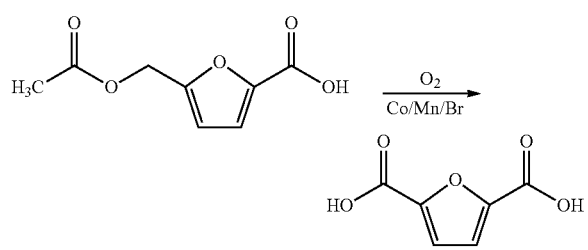

(Formula 17)

Comparative Example 3-2

0.59 g of cobalt acetate ($Co(OAc)_2 \cdot 4H_2O$), 0.58 g of manganese acetate ($Mn(OAc)_2 \cdot 4H_2O$), 0.13 g of sodium bromide, 190 g of acetic anhydride, and 10 g of de-ionized water were added into a high pressure autoclave reactor, and then stirred to be evenly mixed for completely dissolving the catalyst. 3 g of 5-methyl furfural (Formula 4) was then added into the high pressure autoclave reactor. The high pressure autoclave reactor was then sealed with a pressure increased to 20 bar. The mixture in the autoclave reactor was stirred at a rate of 300 rpm and then heated to 130° C. Atmosphere air was then introduced into the mixture at 130° C. for 1 hour, and the mixture was heated to 150° C. and remained at 150° C. for 3 hours. Thereafter, the autoclave reactor was cooled, and pressure of the autoclave was then released. The crude in the autoclave reactor was analyzed by liquid chromatography to determine the conversion rate of 5-methyl furfural being 100%, and the yield of the FDCA (Formula 6) being 43.05%. The above reaction is shown as Formula 18.

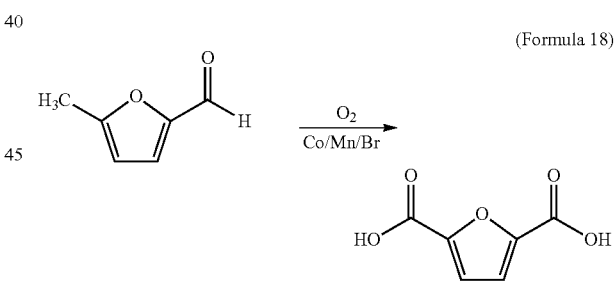

(Formula 18)

Example 3

0.59 g of cobalt acetate ($Co(OAc)_2 \cdot 4H_2O$), 0.58 g of manganese acetate ($Mn(OAc)_2 \cdot 4H_2O$), 0.13 g of sodium bromide, 190 g of acetic anhydride, and 10 g of de-ionized water were added into a high pressure autoclave reactor, and then stirred to be evenly mixed for completely dissolving the catalyst. 1.5 g of 5-(acetoxymethyl)-2-furoic acid (Formula 1 with $R^1$ being methyl group) and 3 g of 5-methyl furfural (Formula 4) were then added into the high pressure autoclave reactor. The high pressure autoclave reactor was then sealed with a pressure increased to 20 bar. The mixture in the autoclave reactor was stirred at a rate of 300 rpm and then heated to 130° C. Atmosphere air was then introduced into the mixture at 130° C. for 1 hour, and the mixture was heated to 150° C. and remained at 150° C. for 3 hours. Thereafter, the autoclave reactor was cooled, and pressure in the autoclave was then released. The crude in the autoclave reactor was analyzed by liquid chromatography to determine the conversion rate of 5-(acetoxymethyl)-2-furoic acid being 99.29%, the conversion rate of 5-methyl furfural being 100%, and the yield of the FDCA (Formula 6) being 46.25%. The above reaction is shown as Formula 19.

(Formula 19)

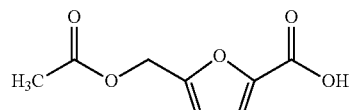
+
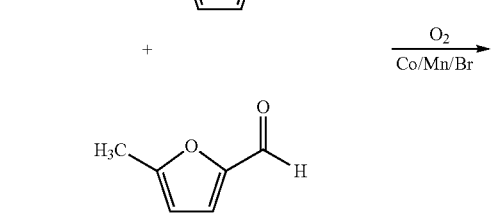
$\xrightarrow{\text{O}_2}{\text{Co/Mn/Br}}$
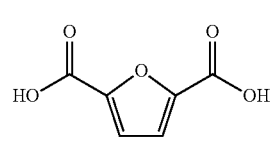

TABLE 3

| | Reactants | Co/Mn/Br Catalyst | Reaction temperature (° C.) | Reaction pressure (bar) | Reactants conversion rate (%) | FDCA selectivity (mole %) | FDCA yield (%) |
|---|---|---|---|---|---|---|---|
| Comparative Example 3-1 | 5-(acetoxymethyl)-2-furoic acid (1.6 wt %) | 0.64 wt % | 130° C. (1 h) + 150° C. (3 h) | 20 | 5-(acetoxymethyl)-2-furoic acid = 99.36 | 40.77 | 40.50 |
| Comparative Example 3-2 | 5-methyl furfural (1.5 wt %) | 0.64 wt % | 130° C. (1 h) + 150° C. (3 h) | 20 | 5-methyl furfural = 100 | 43.05 | 43.05 |
| Example 3 | 5-methyl furfural (1.5 wt %) and 5-(acetoxymethyl)-2-furoic acid (0.73 wt %) | 0.64 wt % | 130° C. (1 h) + 150° C. (3 h) | 20 | 5-methyl furfural = 100, 5-(acetoxymethyl)-2-furoic acid = 99.29 | 46.33 | 46.25 |

As comparison between Comparative Examples 3-1, Comparative Example 3-2, and Example 3, the combination of 5-(acetoxymethyl)-2-furoic acid and 5-methyl furfural in the oxidation process had a higher FDCA selectivity and a higher FDCA yield.

It will be apparent to those skilled in the art that various modifications and variations can be made to the disclosed methods and materials. It is intended that the specification and examples be considered as exemplary only, with a true scope of the disclosure being indicated by the following claims and their equivalents.

What is claimed is:

1. A method for preparing 2,5-furan dicarboxylic acid, comprising:

contacting a furan composition with an oxidant in the presence of a catalyst system, wherein the furan composition includes a first compound and a second compound, the first compound is a compound of Formula 1:

(Formula 1)

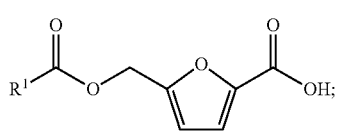

wherein $R^1$ is $C_{1-9}$ alkyl group, wherein the second compound is a compound of Formula 2, a compound of formula 3, a compound of Formula 4, a compound of Formula 5, or a combination thereof;

(Formula 2)

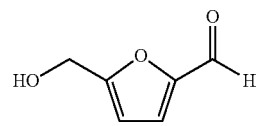

(Formula 3)

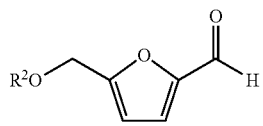

(Formula 4)

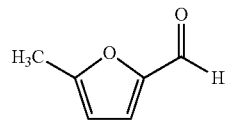

(Formula 5)

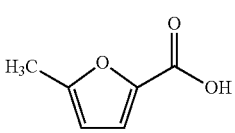

wherein $R^2$ is $C_{1-9}$ alkyl group.

2. The method as claimed in claim 1, wherein the oxidant comprises oxygen.

3. The method as claimed in claim 1, wherein the catalyst system comprises at least one selected from the group consisting of Co(II), Mn(II), Ce(II), a salt thereof, and a combination thereof.

4. The method as claimed in claim 3, wherein the catalyst system comprises a source of bromine.

5. The method as claimed in claim 4, wherein the catalyst system comprises Co(II), Mn(II), and bromide.

6. The method as claimed in claim 4, wherein the catalyst system comprises Ce(II), Mn(II), and bromide.

7. The method as claimed in claim 3, wherein the catalyst system comprises at least one additional metal.

8. The method as claimed in claim 6, wherein the additional metal comprises zirconium, hafnium, copper, nickel, zinc, or a combination thereof.

9. The method as claimed in claim 3, wherein the salt has an anion selected from the group consisting of an acetate, acetate hydrate, bromide, chloride, fluoride, iodide, alkoxide, azide, oxalate, carbonate, carboxylate, hydroxide, nitrate, borate, oxide, acetylacetonate, or a combination thereof.

10. The method as claimed in claim 1, wherein the furan composition is oxidized by the catalyst system and the oxidant under a pressure of 8 bar to 60 bar and at a temperature of 100° C. to 250° C.

11. The method as claimed in claim 1, wherein the furan composition is oxidized by the catalyst system and the oxidant under a pressure of 10 bar to 25 bar and at a temperature of 130° C. to 220° C.

12. The method as claimed in claim 1, wherein $R^1$ is methyl group or ethyl group.

13. The method as claimed in claim 1, wherein the second compound is the compound of Formula 2.

14. The method as claimed in claim 1, wherein the second compound is the compound of Formula 3 with $R^2$ being ethyl group.

15. The method as claimed in claim 1, wherein the second compound is the compound of Formula 4.

16. The method as claimed in claim 1, wherein the first compound and the second compound have a weight ratio of 1:1000000 to 1:0.5.

* * * * *